United States Patent
Lemeshko et al.

(10) Patent No.: US 7,041,647 B2
(45) Date of Patent: May 9, 2006

(54) SYNTHETIC PEPTIDE HAVING AN IONOPHORIC AND ANTIMICROBIAL ACTIVITY

(75) Inventors: Viktor Lemeshko, Medellin (CO); Fanny Guzman, Bogota (CO); Manuel E. Patarroyo, Bogota (CO); Cesar Segura, Medellin (CO); Sergio Orduz, Medellin (CO)

(73) Assignees: Corporacion Para Investigaciones Biologicas, Medellín (CO); Universidad de Antiqquia, Melellín (CO); Fundacion Instituto de Inmunologia de Columbia, Bogotá (CO); Universidad Nacional de Colombia, Bogotá (CO)

( * ) Notice: Subject to any disclaimer, the term of this patent is extended or adjusted under 35 U.S.C. 154(b) by 81 days.

(21) Appl. No.: 10/751,984

(22) Filed: Jan. 7, 2004

(65) Prior Publication Data

US 2005/0043508 A1  Feb. 24, 2005

(30) Foreign Application Priority Data

Apr. 1, 2003  (CO)  .................................. 03-027159

(51) Int. Cl.
*A61K 38/16*  (2006.01)
*C07K 14/00*  (2006.01)
(52) U.S. Cl. ........................................ 514/12; 530/324
(58) Field of Classification Search ................. 514/12; 530/324

See application file for complete search history.

(56) References Cited

U.S. PATENT DOCUMENTS 6,071,877 A * 6/2000 Delecluse et al. ............. 514/12
6,110,464 A * 8/2000 Malvar et al. ........... 424/185.1

OTHER PUBLICATIONS

Orduz et al. Sequence of the cry11Bb1 gene . . . Biochimica et Biophysica Acta. 1998, vol. 1388, pp. 267-272.*

* cited by examiner

*Primary Examiner*—Jeffrey Edwin Russel
(74) *Attorney, Agent, or Firm*—Birch, Stewart, Kolasch & Birch, LLP

(57) ABSTRACT

This invention provides a novel synthetic peptide (P1) of 26 amino acids, which inhibits the microbial growing. Peptide P1 also shows ionophoric activity in rat liver mitochondria. Furthermore, this invention provides pharmaceutical compositions and compositions for agricultural use, which contain the peptide of the invention.

11 Claims, 6 Drawing Sheets

Hemolysis produced by P1 in human red blood cells

SYNTHETIC PEPTIDE HAVING AN IONOPHORIC AND ANTIMICROBIAL ACTIVITY

This Non-provisional application claims priority under 35 U.S.C. § 119(a) on Patent Application No(s). 03-027159 filed in Colombia on Apr. 1, 2003, the entire contents of which are hereby incorporated by reference.

FIELD OF THE INVENTION

The present invention is related with the field of antimicrobial and ionophoric peptides. More specifically, a synthetic peptide, which inhibits the microbial growth, is provided. This peptide also shows ionophoric activity in rat liver mitochondria. Furthermore, pharmaceutical compositions and compositions for agricultural use containing the peptide of the invention are also provided.

BACKGROUND OF THE INVENTION

The cationic antimicrobial peptides are promissory candidates, as new potential antibiotics, with clinical utility. These peptides are produced by both prokaryotic and eukaryotic organisms (Saberwal G., Nagaraj R. 1994. Cell-lytic and antibacterial peptides that act by perturbing the barrier function of membranes: facets of their conformational features, structure-function correlations and membrane-perturbing abilities. *Biochim. Biophys. Acta.* 1197: 109–131; 1. Boman H. G. 1995. Peptide antibiotics and their Role in innate immunity. *Annu. Rev. Immunol.* 13: 61–92; Nicolas P., Mor A. (1995). Peptides as weapons against microorganisms in the chemical defense system of vertebrates. *Annu. Rev. Microbiol.* 4: 277–304; and Maloy W. L., Kari U. P. 1995. Structure-activity studies on magainins and other host defense peptides. *Biopolymers* 37: 105–122). It is known that they are an essential component of the defense system of vertebrates and invertebrates, which are destined to control the cellular multiplication and the invasion of microbial pathogens in organs and tissues (Ganz T. 2002. Antimicrobial peptides in host defense of the respiratory track. *J. Clin. Inv.* 109: 693–697). In view of their therapeutical potential, these natural antibiotics have been the subject matter of many studies in recent years (Hancock R. E. W. and Chapple D. 1999. Peptides antibiotics. *Antimicrob. Agents Chemother.* 43: 1317–1323). The antimicrobial activity of the cationic peptides has been mainly attributed to the disturbance of the cytoplasmic membrane or to the effector function in the natural immunity. The three-dimensional structure of these peptides are highly conserved in spite of the fact that the primary structure is very heterologous (Maloy and Kari 1995, cited article; Hancock R. E. W. 2001. Cationic peptides: effectors in innate immunity and novel antimicrobials. *The Lancet infectious diseases.* 1: 156–164.). These peptides are folded, either forming disulphide bridges or by means of the contact with the lipids of the biological membranes (Bernheimer A. W. 1986. Interactions between membranes and cytolytic peptides. *Biochim. Biophys. Acta.* 864: 123–141.), in an amphiphilic three-dimensional structure wherein the positive charges and the hydrophilic domain are separated from the hydrophobic domain (Hancock, 2001, cited article) leading to the formation of pores with variable selectivity on the membranes of bacteria or eukaryotic cells. The damage of the plasmatic membrane in many cases produces the cellular lysing. Examples of these damages are in U.S. Pat. No. 4,355,104 (October, 1982) and U.S. Pat. No. 4,520,016 (May, 1985) by Hultmark et al., who describe the bacteriolytic properties of some cecropins against Gram-negative bacteria. A very interesting aspect is that the cecropins described in the above patents by Hultmark et al., are not universally effective against all Gram-negative bacteria. For example, the cecropins described lyse bacterium *Serratia marcescens* strain D61108, but not *Serratia marcescens* strain D611. Furthermore, it has been reported that the cecropins do not have lytic activity against eukaryotic cells such as insect cells, liver cells and sheep erythrocytes, as it is observed in the patents by Hultmark and Zasloff U.S. Pat. No. 4,810,777 (March 1989); and in Steiner et al., (Steiner H., Hultmark D., Engstrom A., Bennich H., Boman H. G. 1981. Sequence and specificity of two antibacterial proteins involved in insect immunity. *Nature.* 292: 246–248), Andreu et al., (Andreu D., Merrifield R. B., Steiner H., Boman H. G. 1985. N-terminal analogues of cecropin A: synthesis, antibacterial activity, and conformational properties. *Biochemistry.* 24: 1683–1688.) and Boman et al., (Boman H. G., Faye I., von Hofsten P., Kockum K., Lee J. Y., Xanthopoulos K. G., Bennich H., Engstrom A., Merrifield R. B., Andreu D. 1985. On the primary structures of lysozyme, cecropins and attacins from *Hyalophora cecropia*. *Dev. Comp. Immunol.* 9: 551–558.). More recently, a group of antimicrobial peptides produced by human tissues and known as defensins has been reported in the patents by Barra, et al., U.S. Pat. No. 6,310,176 (October 2001), and Olsen et al., U.S. Pat. No. 6,420,116 (July 2002).

Other peptides with the same properties are naturally produced in the immunological system of the insects *Sarcophaga peregrina* and *Bombyx mori*, as they were reported by Nakajima et al. (Nakajima Y., Qu X. M., Natori S. 1987. Interaction between liposomes and sarcotoxin IA, a potent antibacterial protein of *Sarcophaga peregrina* (flesh fly). *J. Biol. Chem.* 262: 1665–9). The differences in the bacteriolytic activity of the antimicrobial peptides have been attributed to the differences in the composition of the cell plasma membranes (Bernheimer, 1986, cited article). Therefore, it is not surprising that less specific peptides such as the cecropins have more capacity for lysing prokaryotic cells than the eukaryotic cells of the insect.

SUMMARY OF THE INVENTION

In a first embodiment, the present invention provides a new peptide, with the following sequence of amino acids: VAPIAKYLATALAKWALKQGFAKLKS (SEQ ID NO: 1) and pharmaceutically acceptable salts or derivatives thereof.

This new synthetic peptide has a cationic nature. This peptide with a length of 26 amino acids, named P1, can kill bacteria by contact with them. The peptide of this invention also induces a high permeability of the inner mitochondrial membrane for potassium and hydrogen ions, causing a dramatic swelling when incubated in the isotonic media containing $KNO_3$ and $NH_4NO_3$, respectively, at micro molar concentrations of the peptide, comparable to the effective concentrations of valinomycin (a classical ionophore for potassium) and carbonyl-cyanide-p-trifluoromethoxy phenylhydrazone (FCCP, a classical protonophore). In the mitochondria, the ionophoric activity of the peptide is selective for cations, with the following order of selectivity: $H^+>K^+>Na^+>Tris^+$. The ionophoric activity of P1 suggests that this peptide could be a potential antibiotic. The structure of P1 in a hydrophobic environment is an alpha-helix, which is in agreement with the idea according to which the peptide can form ionic channels in the biological membranes. The hemolytic activity of peptide P1 is highly susceptible to the composition of the incubating media. In a physiological solution, its hemolytic activity decreases significantly with an increase in the hematocryte and it was observed that it is insignificant when the hematocryte is high.

The peptide of the present invention is useful in the inhibition of the microbial growth. Furthermore, said peptide shows an ionophoric activity in mitochondria. Particularly, the peptide of the present invention exhibits antimicrobial activity against Gram-positive and Gram-negative bacteria. In the same way, said peptide exhibits ionophoric activity in the inner membrane of rat liver mitochondria.

The present invention also provides the use of the peptide in the manufacture of a drug or pharmaceutical composition having antimicrobial activity.

In a second embodiment, the present invention provides a pharmaceutical composition, which comprises the peptide of the present invention as an active principle, together with a pharmaceutically acceptable carrier.

In a third embodiment, the present invention provides a pharmaceutical composition comprising as an active principle the peptide of the present invention in an amount effective for inhibition of the microbial growth, together with a pharmaceutically acceptable carrier.

In a fourth embodiment, the pharmaceutical composition of the present invention is provided in a form suitable for oral, topical, rectal or parenteral administration.

The present invention also provides, as a fifth embodiment, the use of the peptide in the manufacture of a composition for agricultural use.

In a sixth embodiment, the present invention provides a composition for agricultural use, which comprises as active ingredient the peptide of the present invention together with an acceptable carrier.

In a seventh embodiment, the present invention provides a composition for agricultural use, which comprises as active ingredient the peptide of the present invention in an amount effective for inhibition of microbial growth, together with an acceptable carrier.

In an eighth embodiment, the composition for agricultural use of the present invention is provided in a form suitable for its agricultural application.

DETAILED DESCRIPTION OF THE INVENTION

Figure 1:
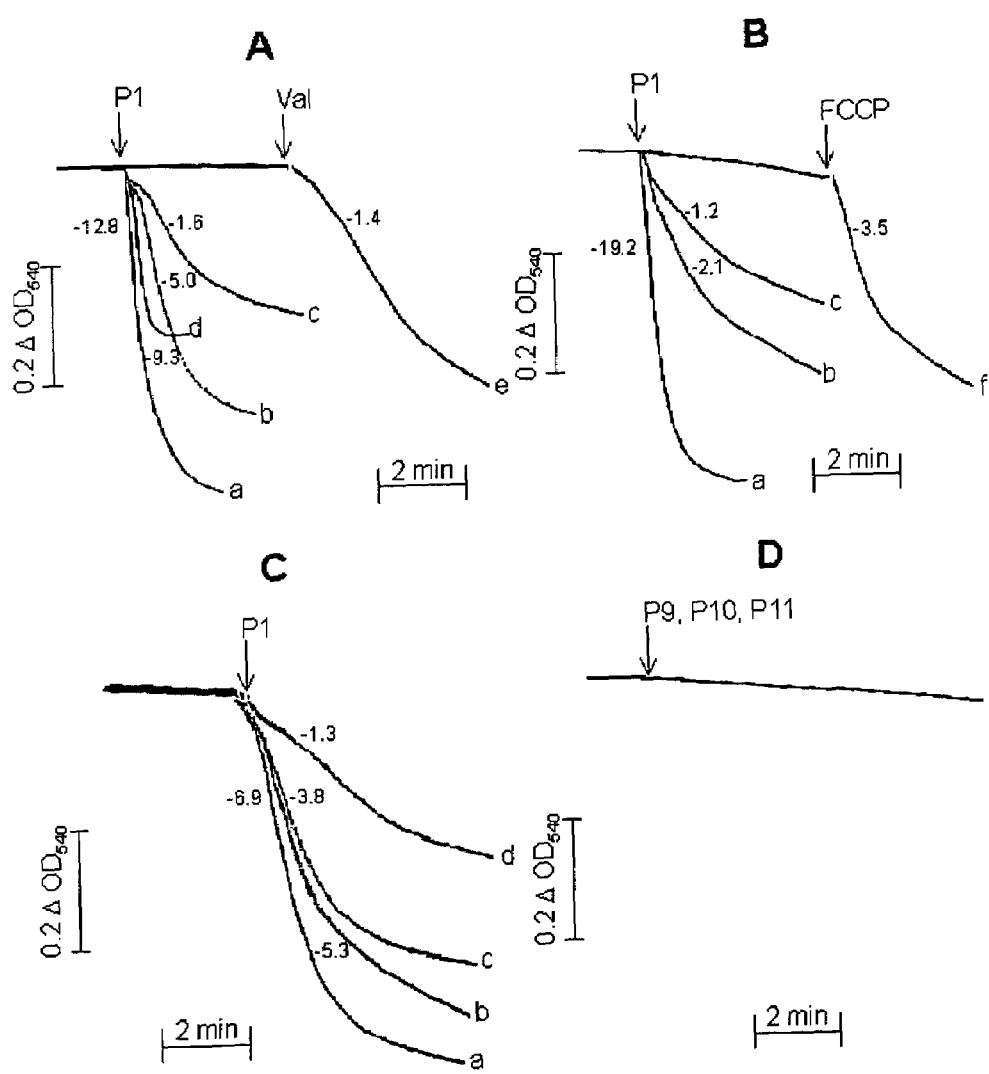
FIG. 1 Ionophoric activity of P1 in the inner membrane of rat liver mitochondria. The mitochondria at a concentration of 0.5 mg/ml of protein were incubated in the media 125 mM $KNO_3$, 5 mM HEPES-tris, pH 7.4 (Panel A) and 125 mM $NH_4NO_3$, 5 mM HEPES-tris, pH 7.4 (Panel B), both media were supplemented with 2.5 μM rotenone and 1 μM oligomycin (RO), added just after the mitochondria. The peptide P1 was added at the following final concentrations: 1.8 μM of P1 (curves a); 0.36 μM of P1 (curves b); 0.18 μM of P1 (curves c); 0.18 μM of P1 plus 2.5 mM of succinate (curves d); 0.12 μM of valinomycin (curve e), and 2 μM of FCCP, (curve f). In Panel C, the permeability of the inner mitochondrial membrane induced by the peptide P1 was evaluated for the following cations: $H^+$, $K^+$, $Na^+$, and $Tris^+$. By the addition of 0.18 μM of P1 to the mitochondria plus RO in the following media, respectively: 125 mM $NH_4NO_3$, 5 mM HEPES-tris, pH 7.4 (curve a); 125 mM $KNO_3$, 5 mM HEPES-tris, pH 7.4, (curve b); 125 mM $NaNO_3$, 5 mM HEPES-tris, pH 7.4, (curve c); and 125 mM Tris-HCl, 5 mM HEPES-tris, pH 7.4, (curve d). Ionophoric activity was not observed when other peptides were tested with mitochondria in the medium 125 mM $NH_4NO_3$, 5 mM HEPES-tris, pH 7.4 (peptides P9, P10 and P11)(FIG. 1, Panel D).

Synthetic peptide P1 of the present invention is comprised by 26 amino acids. The natural existence of this peptide in bacteria and animals has not been reported in the literature. The data herein provided indicate that peptide P1 is a new bactericide factor. In view of its proved antimicrobial activity against Gram-positive and Gram-negative bacteria, together with its ionophoric activity in the mitochondria, peptide P1 constitutes an antimicrobial peptide, taking into consideration that the term "antimicrobial" as it is used herein means that the peptide of the present invention can inhibit, prevent, or destroy the growth or multiplication of the microorganisms presented herein and others.

The term "contact" mentioned in the section of antimicrobial assays makes reference to the exposure of the bacteria to the peptide in such a way that the peptide permeabilizes effectively the outer membrane of the Gram-negative and Gram-positive bacteria, killing them. The contact can be in vitro, for example, by means of the addition of the peptide to a bacterial culture in order to test the susceptibility of the bacteria to the peptide. Examples of the bacteria, which can be killed or whose growth can be inhibited by means of peptide P1 include: *Escherichia coli, Staphylococcus aureus, Streptococcus pneumoniae, Haemophilus influenzae, Enterococcus faecalis, Bacillus subtilis, Bacteroides fragilis* and *Clostridium perfringens*, among others.

Peptide P1 has an amphipatic character, which allows it to form helicoidal structure when it is in the hydrophobic environment of the biological membranes. The cationic charge (positive) of peptide P1 is determined by the amino acids located in the positions 6, 14, 18, 23 and 25, therefore, the total positive charges is "of plus five" (+5). The residues of amino acids 6, 10, 14, 18, 19, 23, 25 and 26 are hydrophilic, while the residues of amino acids 1, 2, 3, 4, 5, 7, 8, 9, 11, 12, 13, 15, 16, 17, 20, 21, 22, 24 are all hydrophobic residues.

According to the above-presented data, the peptide indicated as P1 can contact bacterial cells, killing them by an increase in the permeability of their plasma membranes. The cells include microorganisms Gram-positive as well as Gram-negative. Peptide P1 has 26 amino acids; at least one portion could adopt the alpha-helix conformation. The peptide has a substantially hydrophilic head with a positive charge and a substantially hydrophobic tail. The peptide can adopt the alpha-helix conformation in a medium of increasing hydrophobicity (increases in the percentage of TFE) and in a hydrophobic medium of an artificial membrane. The conformation can have a predominantly hydrophobic face along the helicoidal structural and a hydrophilic part in the opposite. The peptide reveals the ionophoric activity in rat liver mitochondria. This activity was comparable to the one of valinomycin (an antibiotic selective for $K^+$ used in many studies) and FCCP (one of the classical protonophores).

With respect to the expression "derivatives thereof", it is well known in regard to the technical area to which the present invention pertains that minor amino acid substitutions can be made to the peptide, which do not affect or do not substantially affect the function of the peptide. Such substitutions can be accomplished according to procedures well known to those skilled in the art. Thus, all peptides having substantially the same amino acid sequence, and substantially the same antimicrobial or ionophoric activity, are within the scope of this invention.

Also within the scope of the present invention are pharmaceutically acceptable salts of the peptide of this invention. Such salts are formed by methods well known to skilled artisans. Thus, when in the instant disclosure including the claims the term peptide is used said term is intended to include both derivatives and pharmaceutically acceptable salts of the peptide.

In the same way, the peptide according to the present invention can be formulated for use in human or veterinary medicine for therapeutic or prophylactic use. The pharmaceutical compositions which include the peptide of the present invention can be administered orally, rectally or parenterally, selecting in each case the pharmaceutically acceptable carriers more suitable depending of the selected dosage form. The administration may also take the form of topical application.

In the same way, the peptide of the present invention can be formulated for its use in agriculture. The compositions for agricultural use, which include the peptide of the present invention, can be applied in several forms over several types of formulations, selecting in each case the acceptable carriers more suitable for the selected application way, or a synthetic gene can be used to develop transgenic plants.

The following examples and methods are indicated in order to the herein described invention can be more completely understood. It should be understood that these methods and examples are only for illustrative purposes and they cannot be interpreted as limiting this invention in any way.

PREPARATION METHODS AND ACTIVITY ASSAYS

Method 1. Isolation of Mitochondria:

Male rats were beheaded, their livers were extracted and placed in 45 ml of a cold solution composed of 210 mM Mannitol, 70 mM Saccharose, 1 mM EGTA, 5 mM HEPES-tris, pH 7.4 (GMSH). The livers were homogenized with an automatic Dounce homogenizer containing a Teflon pestle. The homogenate was centrifuged at 600×g for 10 min at 4° C. (Centrifugal machine Jouan, MR1812). The supernatant was decanted and centrifuged at 10000×g for 10 min at 4° C. The mitochondrial pellet was re-suspended in 30 ml of a cold solution composed of 210 mM Mannitol, 70 mM Saccharose, 20 µM EGTA, 5 mM HEPES-tris, pH 7.4 (MSHG) and centrifuged again at 10000×g for 10 min at 4° C. The final bottom of mitochondria was re-suspended in buffer MSHG at a final concentration of mitochondrial protein of 60–80 mg/ml.

Method 2. Chemical Synthesis of Peptides:

The peptides were synthesized by the method of solid phase synthesis (Merrifield B. 1963. Solid Phase Peptide Synthesis, Journal American Chemical Society. 85: 2149–2154; and Houghten R. A. 1985. General methods for the rapid solid phase synthesis of large numbers of peptides: specificity of antigen antibody interaction at the level of individual amino acids. *Proc. Natl. Acad. Sci. USA.* 82: 5131–5135.) under the methods of good manufacture practices (GMP). A resin p-methyl benzidrylamine (MBHA) (0.7 meq/g), t-boc amino acids (Bachem, USA) and the process of high-low cleavage were used in the synthesis. (Andreu D, Merrifield RB, Steiner H, Boman HG. 1983. Solid-phase synthesis of Cecropin A and Related Peptides. *Proc. Natl. Acad. Sci USA* 80: 6475–6479.). Once synthesized, the peptides were extracted with 10% acetic acid in water. The peptides were purified by high pressure liquid chromatography (HPLC), in a reverse phase column, and they were analyzed by means of mass spectrometry (Maldi-Tof). The peptides were lyophilized and kept in powder at 4° C. until its use. Peptide P1 is highly soluble in aqueous solutions.

Method 3. Assays of Mitochondrial Swelling in Isotonic Media

The mitochondria were isolated and prepared as described above. The mitochondria were resuspended at a concentration of mitochondrial protein of 0.5 mg/ml in 1 ml of different isotonic media: 125 mM $NH_4NO_3$, 5 mM HEPES-tris, pH 7.4; 125 mM $KNO_3$, 5 mM HEPES-tris, pH 7.4; 125 mM Tris-$NO_3$, 5 mM HEPES-tris, pH 7.4; 125 mM $NaNO_3$, 5 mM HEPES-tris, pH 7.4. The addition of mitochondria was immediately followed by the addition of 2.5 µM rotenone and 1 µM oligomycin (RO). After 1 min of incubation at room temperature, the peptide was added to the mitochondria at the concentrations indicated in FIG. 1. The mitochondrial swelling was spectrophotometrically monitored at 540 nm (Turner Spectrophotometer, model SP-850, USA, modified with a magnetic mini-stirrer). The curves were recorded in a graphical recorder (Linseis model L250E, USA), scanned and then processed in the program Adobe Photoshop V5.0.

Method 4. Assay of Antimicrobial Activity:

The following bacteria were tested: *Escherichia coli* (ATCC 25922) and *Staphylococcus aureus* (ATCC 25923) were grown in Mueller Hinton; *Streptococcus pneumoniae* (ATCC 49619) was grown Mueller Hinton supplemnted with 5% sheep blood; *Haemophylus influenzae* (ATCC 49247) was grown in HTM; *Enterococcus faecalis* (ATCC 29212), *Bacillus subtilis* (ATCC 6633) and *Bacillus anthracis* were grown in Mueller Hinton; *Bacteroides fragilis* (ATCC 25285) and *Clostridium perfringens* (ATCC 13124) were grown in Brucella agar supplemented with 5% blood, hemin and vitamin K; *Pseudomonas aeruginosa* (ATCC 27603) and *Pseudomonas aeruginosa* (Multi-Resistant) were grown in Mueller Hinton; and *Klebsiella pneumoniae* (ATCC 70603) was grown in BHI. The bacterial strains were grown in the corresponding cultures media, until they reached logarithm phase (4–6 h) at a $OD_{600}$=1.0. The culture medium was removed by centrifugation at 10000 rpm for 10 min at 4° C. and the bottom, containing the bacterial cells, was washed twice in a buffer containing 25 mM $Na_2PO_4$, 25 mM $NaHPO_4$, 150 mM NaCl, 5 mM KCl, pH 7.4 (PBS). The bacteria were adjusted at an $OD_{600}$=0.2 in the same buffer (5000–10000 cells/ml). The in vitro antibacterial activity of the peptide was measured as follows: 500 µl of the bacterial suspension were treated with 7.1 µM of P1 for 2 h at 37° C. in 1.5 ml Eppendorf tubes. After incubation, the cells were washed in the same volume of buffer and then plated in Petri dishes with adequated culture media; after 24 h of incubation at 37° C., the colony forming units were determined. The percentage of growth inhibition was obtained comparing the number of colony forming units incubated with the peptide to the colony forming units of the treatment without the peptide.

Figure 3:
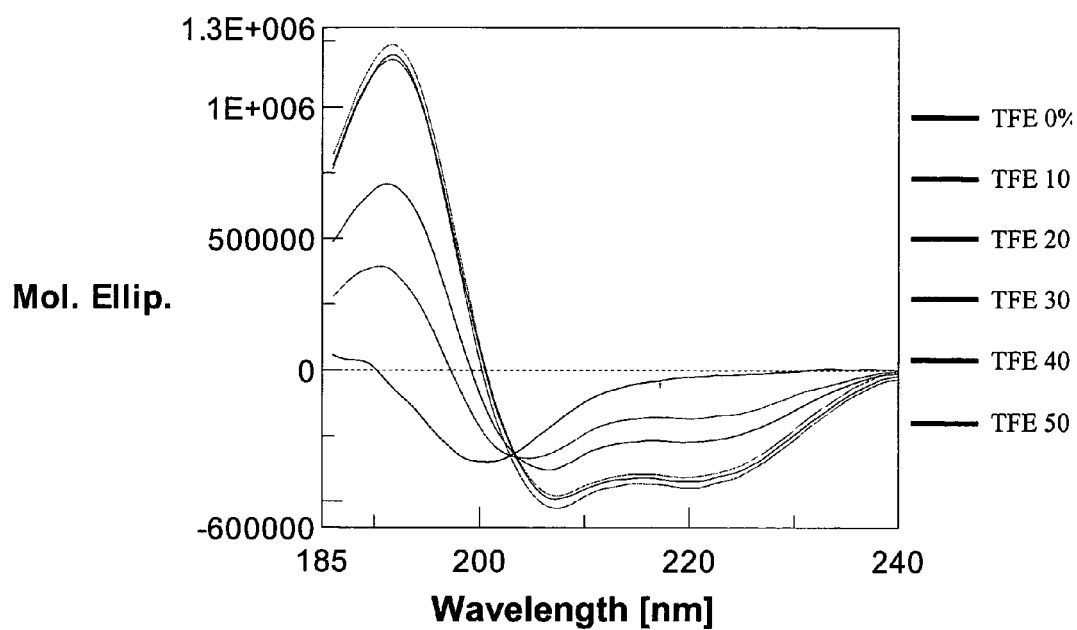
FIG. 3 Spectrum of circular dicroism of P1 in a hydrophobic medium; The figure shows that a larger part of the peptide adopts an helicoidal conformation in a medium of increasing hydrophobicity (in increasing concentrations of trifluoroethanol, TFE). The percentages of alpha-helix structure of peptide P1 are showed in Table 3.
Figure 4:
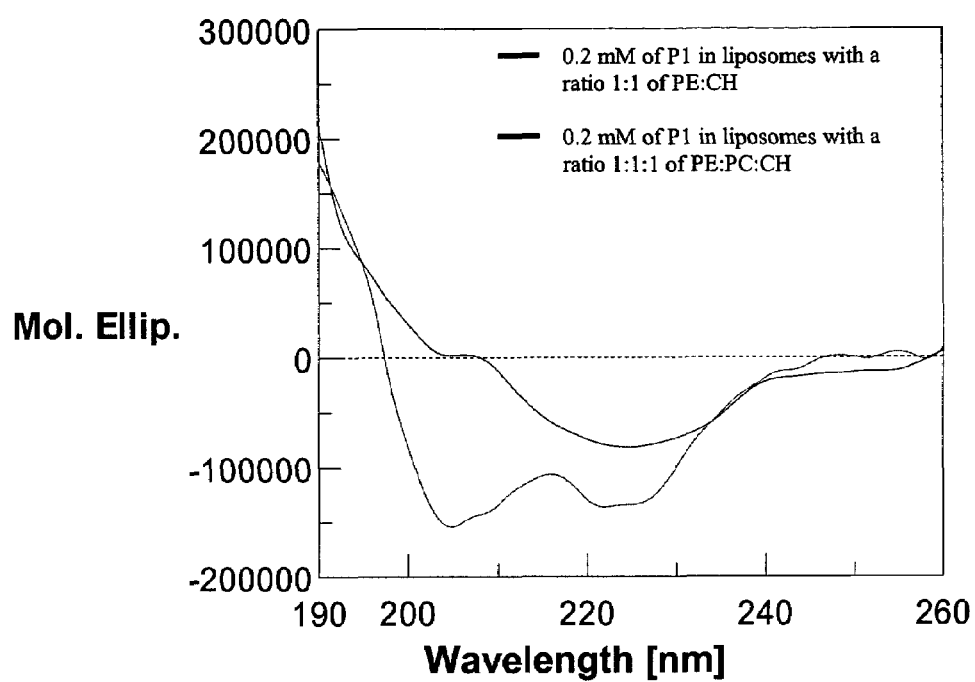
FIG. 4 Spectrum of circular dicroism of peptide P1 in artificial membranes. The liposomes were prepared as described in materials and methods. The figure shows that peptide P1 can adopt helicoidal conformation in the hydrophobic media of an artificial membrane composed of phospholipids and cholesterol.
Figure 5:
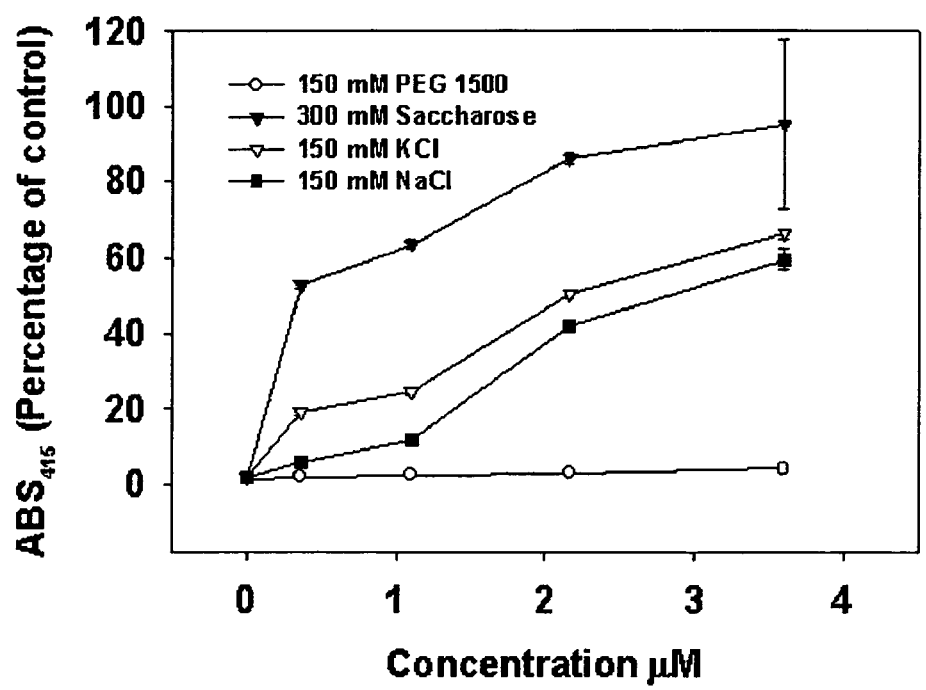
FIG. 5 Effect of P1 in human red blood cells; Human red blood cells were resuspended to a hematocryte of 0.5% in the isotonic solutions indicated in materials and methods. The peptide P1 was added at different concentrations to the cellular suspensions and incubated for 1 hour at room temperature. The supernatants were obtained by centrifugation of the suspensions at 10000 rpm for 5 min at 4° C. (International Equipment Company IEC, Centra MP4R; rotor 851), the absorbance of the supernatants was registered at 415 nm with a spectrophotometer (BIORAD). The results were expressed as percentage of hemolysis relative to the maximum hemolysis (erythrocytes hemolysed in 0.01% Tween-20).
Figure 6:
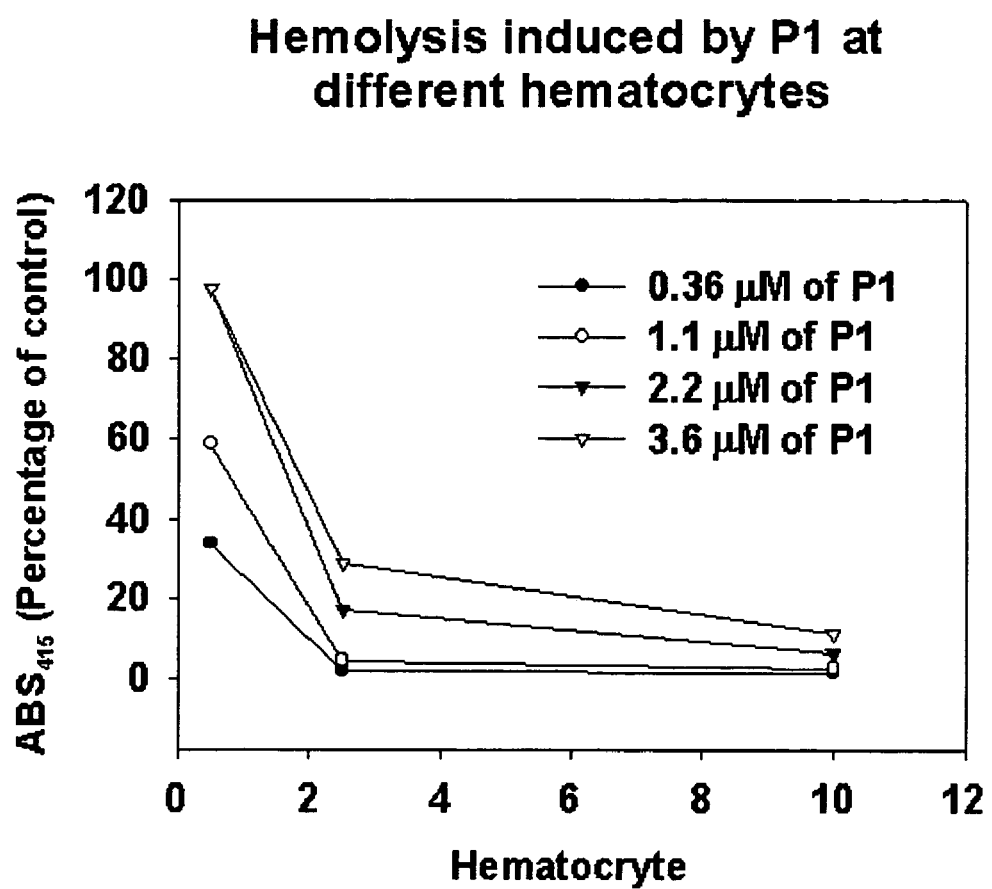
FIG. 6 The hemolysis caused by P1 in the erythrocytes decreases with an increase in the hematocryte; human red blood cells were resuspended at different hematocrytes: 0.5%, 2.5% and 10% in 150 mM NaCl, 5 mM KCl, 5 mM Glucose, 10 mM HEPES-tris, pH 7.4. Peptide P1 was added at different concentrations in the cellular suspension and incubated during 1 h at room temperature. The supernatants were obtained by centrifugation at 10000 rpm for 5 min at 4° C. and the absorbance at 415 nm was determined with a BIORAD spectrophotometer. The results were expressed as percentage of hemolysis relative to the maximum hemolysis (erythrocytes lysed in 0.01% Tween-20).

Method 5. Hemolytic Activity of Peptide P1:

The hemolytic activity of peptide P1 was determined in heparinized human red blood cells from a volunteer (final concentration of heparin 20.4 U/ml), and washed three times in 150 mM NaCl, 9 mM $Na_2PO_4$, pH 7.3, at room temperature. The red blood cells were resuspended to an hematocryte of 0.5% in isotonic solutions 150 mM NaCl, 5 mM KCl, 5 mM Glucose, 10 mM HEPES-tris, pH 7.4; 155 mM KCl, 5 mM Glucose, 10 mM HEPES-tris, pH 7.4; 300 mM saccharose, 5 mM KCl, 5 mM Glucose, 10 mM HEPES-tris, pH 7.4; 150 mM polyethyleneglycol-1500 (PEG-1500), 5 mM KCl, 5 mM Glucose, 10 mM HEPES-tris, pH 7.4. The peptide was dissolved at a concentration of 2 mg/ml in 5 mM KCl, 5 mM Glucose, 10 mM HEPES-Tris, pH 7.4, and two final concentrations of 0.6 µM and 3.6 µM of P1 were added to the cellular suspension (Table 2), and incubated for 1 h at room temperature. The supernatants were recovered by centrifugation of the cellular suspension at 10000 rpm for 5 min at 4° C. and the absorbance at 415 nm was determined in a BIORAD spectrophotometer. The averages and standard deviations were calculated and the data were introduced to the program SigmaPlot V4.0 in order to generate the corresponding graphs (FIGS. 3 and 4).

Method 6. Preparation of Liposomes and Circular Dicroism (CD):

The liposomes were prepared as follows: the lipids: phosphatidylcholine (PC), phosphatidylethanolamine (PE) and cholesterol (CH) were dissolved in chloroform at the following molar ratios: 1:1:1 PC:PE:CH and 1:1 PC:CH (liposomes with ratios corresponding to a biological membrane). Then, the solvent was removed by evaporation and dried at high vaccum for 8 h. The lipid mixture was rehydrated at a final concentration of 100 mM in 25 mM $Na_2PO_4$, 25 mM $NaHPO_4$, 150 mM NaCl, 5 mM KCl, pH 7.4 (PBS). The liposomes were homogenized by sonication (Sonicator Branson) for 1 h. The liposomes and the peptide were mixed as follows: 50 mM phospholipids (liposomes), 0.2 µM of peptide P1 in PBS, for 1 h at 5° C. The data were taken in the spectropolarimeter (Jasco J-810).

All reagents with analytical grade were obtained from Sigma Chemical Co. (St Louis Mo. USA).

BIOLOGICAL ASSAYS

EXAMPLE 1

Ionophoric Activity in Rat Liver Mitochondria

Ionophoric effect of P1 in the inner rat liver mitochondrial membrane; P1 induces a strong swelling of rat liver mitochondria due to its ionophoric activity. This activity was determined in mitochondria suspended in an isotonic medium composed of 125 mM $KNO_3$, 5 mM HEPES-tris, pH 7.4 (FIG. 1, Panel A), and 125 mM $NH_4NO_3$, 5 mM HEPES-tris, pH 7.4 (FIG. 1, Panel B) at different final concentrations of P1 (traces a, b, and c in FIG. 1, Panels A and B). The rate of mitochondrial swelling induced by P1 (indicated by the slopes of the curves) shows to be comparable to those observed with valinomycin (slope=1.6 with 0.18 µM of P1 and slope=1.4 with 0.12 µM valinomycin, FIG. 1, Panel A, curves c and e respectively) in the medium 125 mM KNO3, 5 mM HEPES-tris, pH 7.4. A significant increase in the mitochondrial swelling was observed when the mitochondria were energized (slope=1.6 with 0.18 µM of P1 and slope=9.3 with 0.18 µM of P1 plus 2.5 mM of succinate) (FIG. 1, Panel A, curves c and d, respectively). In the same way, the speed of swelling induced by P1 was comparable to the one induced by the uncoupler FCCP (slope=2.1 with 0.36 µM of P1 and slope=3.5 with 2 µM FCCP) (FIG. 1, Panel B, curves b and f, respectively) in the medium 125 mM $NH_4NO_3$, 5 mM HEPES-tris, pH 7.4. The ionophoric activity of P1 was also monitored in other isotonic media: 125 mM Tris-$NO_3$, 5 mM HEPES-tris, pH 7.4; and 125 mM $NaNO_3$, 5 mM HEPES-tris, pH 7.4. The rate of mitochondrial swelling was different depending upon the isotonic medium used, with the rate order $NH_4NO_3$>$KNO_3$>$NaNO_3$>tris-$NO_3$ (FIG. 1, Panel C, slopes in curves a, b, c, and d, respectively). The results indicated that P1 induces a high permeability of the inner mitochondria membrane for cations, and that the permeabilizing effect of P1 is comparable to the one of valinomycin and FCCP. FIG. 1, Panel D, shows the curves obtained with other synthetic peptides (P9 with 14 amino acids, P10 with 32 amino acids and P11 with 29 amino acids). Other tested peptides were: P2 with 24 amino acids, P3 with 17 amino acids, P6 with 19 amino acids, P8 with 23 amino acids, and P12 with 18 amino acids.

EXAMPLE 2

Figure 2:
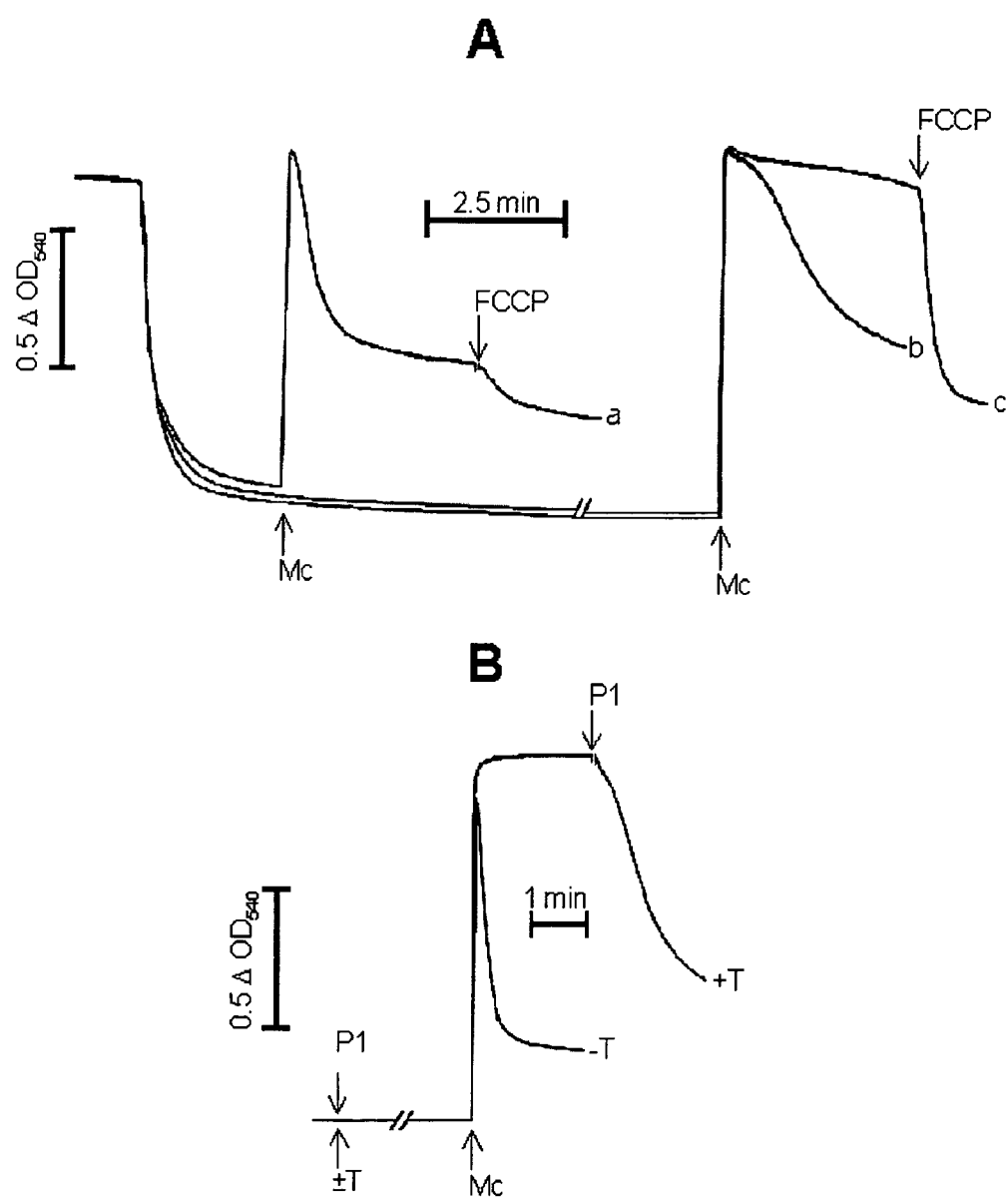
FIG. 2. The ionophoric activity of P1 in the inner membrane of rat liver mitochondria is susceptible to proteases; In this assay, 0.5 mg/ml of mitochondrial protein were incubated with RO and 1.8 μM of P1 during different intervals of time: 2.5 min (curve a); 10 min (curve b); 20 min (curve c), then, new fresh mitochondria (0.5 mg/ml) were added (Panel A). The ionophoric effect of P1 disappeared when P1 was previously treated with trypsin (B) thus: 1.8 μM of P1 and 10 μg/1 ml of trypsin were incubated for 5 min at room temperature, then 0.5 mg/ml of mitochondria were added (curve +T), the peptide without treatment with trypsin is indicated (curve −T, P1).

Effect of the proteases over the ionophoric activity of P1 in the mitochondria; It is well known that the mitochondria have their own proteases, which are released at the moment of their swelling. The mitochondria and peptide P1 (1.8 µM)

were incubated in the medium 125 mM $NH_4NO_3$, 5 mM HEPES-tris, pH 7.4. After 2.5, 10 and 20 minutes, new fresh mitochondria (0.5 mg/ml) were added and the resulting slopes were recorded at 540 nm and were compared. FIG. 2, Panel A, shows that after 2.5 min, P1 shows ionophoric activity (FIG. 2, Panel A, curve a), this activity decreases after 10 min of incubation (FIG. 2, Panel A, curve b) and the activity disappears after 20 min (FIG. 2, Panel A, curve c). This experiment indicates that the ionophoric activity of P1 is transitory. One explanation is that peptide P1 is sensitive to proteases. In order to prove this, P1 was treated with trypsin (see legend of FIG. 2), and it was observed that the treatment of peptide P1 with trypsin suppresses its ionophoric activity in mitochondria (FIG. 2, Panel B, curve +T).

EXAMPLE 3

Antimicrobial activity; The peptide P1 is able of killing bacteria: The growth of *Escherichia coli* (ATCC 25922), *Staphylococcus aureus* (ATCC 25923), *Streptococcus pneumoniae* (ATCC 49619), *Bacteroides fragilis* (ATCC 25285), *Enterococcus faecalis* (ATCC 29212) and *Clostridium perfringens* (ATCC 13124) were completely inhibited (100%) with 7.1 µM of peptide P1. *Haemophylus influenzae* (ATCC 49247), *Pseudomonas aeruginosa* (ATCC 27603) and a strain of *Pseudomonas aeruginosa* multiresistant to antibiotics were susceptible to the same concentration of the peptide (7.1 µM) with a percentage of growth inhibition between 76% and 86%. Finally, *Klebsiella pneumoniae* (ATCC 70603) and the group of *Bacillus* including: *Bacillus subtilis* (ATCC 6633) and *Bacillus anthracis*, were less susceptible to the peptide concentration of 7.1 µM with a percentage of growth inhibition between 30.8% and 40%. Table 1 shows the antimicrobial spectrum of peptide P1.

TABLE 1

Antimicrobial activity of peptide P1

| Bacterium | Strain | Dose µM | % of growth inhibition |
|---|---|---|---|
| *Escherichia coli* | ATCC 25922 | 7.1 | 100 |
| *Staphylococcus aureus* | ATCC 25923 | 7.1 | 100 |
| *Streptococcus pneumoniae* | ATCC 49619 | 7.1 | 100 |
| *Haemophylus influenzae* | ATCC 49247 | 7.1 | 76 |
| *Enterococcus faecalis* | ATCC 29212 | 7.1 | 99.6 |
| *Bacillus subtilis* | ATCC 6633 | 7.1 | 30.8 |
| *Bacillus anthracis* | | 7.1 | 40 |
| *Bacteroides fragilis* | ATCC25285 | 7.1 | 100 |
| *Clostridium perfringens* | ATCC13124 | 7.1 | 100 |
| *Pseudomonas aeruginosa* | ATCC27603 | 7.1 | 80 |
| *Pseudomonas aeruginosa* | (Multi-Resistant) | 7.1 | 86 |
| *Klebsiella pneumoniae* | ATCC70603 | 7.1 | 39 |

EXAMPLE 4

Hemolytic activity; Based in the absence or in the presence of hemolytic activity, the peptides can be classified as antibiotic or cytotoxic peptides. The cytotoxic potential of P1 was determined in human red blood cells. The hemolytic activity was observed in isotonic media with saccharose, KCl and NaCl, being the permeability order for saccharose>KCl>NaCl at the concentration of the peptide of 0.36 µM. This order of selectivity disappears when the concentration of the peptide was increased to 3.6 µM indicating that this peptide concentration is saturated in the used conditions. On the contrary, in isotonic medium PEG-1500, peptide P1 does not show hemolytic activity. Table 2 and FIG. 3 show the hemolytic activity of peptide P1. It is interesting that the hemolytic activity decreases dramatically when the hematocryte was increased at 10%, well below the normal values, indicating that the peptide could be an antimicrobial peptide with very low or no cytotoxic activity (FIG. 4).

TABLE 2

Hemolytic activity of peptide P1 in human erythrocytes

| | Percentage of hemolysis | |
|---|---|---|
| Isotonic Media | 0.36 µM P1 $\bar{X}$ ± SD | 3.6 µM P1 $\bar{X}$ ± SD |
| PEG-1500 150 mM | 0.25 ± 0.07 | 2.75 ± 0.3 |
| Saccharose 150 mM | 57.5 ± 0.73 | 75.5 ± 10.38 |
| KCl 150 mM | 17.25 ± 1.05 | 64.25 ± 1.23 |
| NaCl 150 mM | 3.75 ± 0.05 | 59.25 ± 1.15 |

EXAMPLE 5

Structure of peptide P1; The structure in solution of peptide P1 was studied by means of the spectroscopic method circular dicroism (CD). This is a type of absorption spectroscopy, which can provide information on the structure of many types of biological macromolecules. The phenomenon of circular dicroism is very sensitive to the secondary structure of the polypeptides. In an aqueous environment, peptide P1 has predominantly a random conformation (Table 3). The contents (expressed in percentage) of the organized structure of peptide P1 is increased with the increase of the concentration of trifluoroethanol (TFE); these data indicate that in a medium with higher hydrophobicity, peptide P1 adopts preferentially an helicoidal conformation (FIG. 3). The stabilizer effect of TFE is suggested by the preference of the molecules of TFE to aggregate around the peptide. As a consequence of this effect, the water around the peptide is displaced, removing the hydrogen bridges, which provide a low dielectric environment. This, in its turn, favors the formation of hydrogen bridges in the inner side of the peptide and, therefore, the structure of alpha helix (Roccatano D., Colombo G., Fioroni M., and. Mark A. E. 2002. Mechanism by which 2,2,2-trifluoroethanol water mixtures stabilize secondary-structure formation in peptides: A molecular dynamics study. *Proc. Natl. Acad. Sci. USA*. 99: 12179–12184.). Anyway, the structure of the peptide in TFE can be different to the one which can be formed in the hydrophobic environment of a biological membrane, wherein the peptide interacts with lipids. This is the reason for performing the experiments with liposomes. FIG. 4 shows the CD spectrum of peptide P1 in the hydrophobic environment of two types of liposomal membranes. The liposomes prepared in the molar ratios 1:1:1 in PC, PE and CH or 1:1 in PC:CH can resemble the lipid composition of a biological membrane. The CD spectrum reveals that peptide P1 can adopt an alpha-helicoidal conformation when it interacts with the lipids of the liposomes (FIG. 4). In these experiments, the peptide attached preferentially to the liposomes with a larger ratio of cholesterol (1:1 PC:CH).

TABLE 3

Spectrum of circular dicroism of peptide P1 in a medium with growing hydrophobicity (% de TFE).

| | % secondary structure (fraction) | | | | % Total |
|---|---|---|---|---|---|
| % TFE* | Helix | Beta | Loop | Disordered | (fraction) |
| 0 | 0.0 (474.6) | 27.3 (474.6) | 11.4 (198.2) | 61.3 (1066.1) | 100.0 (1738.9) |
| 10 | 19.4 (407.5) | 33.1 (697.3) | 0.0 (0) | 47.5 (999.3) | 100.0 (2104.1) |
| 20 | 40.5 (829.9) | 17.6 (360.2) | 0.0 (0) | 42.0 (861.4) | 100.0 (2051.4) |
| 30 | 54.6 (1456.1) | 9.6 (256.9) | 0.0 (0) | 35.7 (951.9) | 100.0 (2664.9) |
| 40 | 68.2 (1479.4) | 0.0 (0) | 0.0 (0) | 31.8 (688.2) | 100.0 (2167.6) |
| 50 | 65.2 (1455.7) | 0.0 (0) | 0.0 (0) | 34.8 (777.9) | 100.0 (2233.5) |

*TFE Trifluoroethanol diluted in pure water ($H_2O$) at the indicated concentrations, the final concentration of the peptide was 0.18 µM.

SEQUENCE OF THE PEPTIDE OF THE PRESENT INVENTION

General Information
CHARACTERISTICS OF THE SEQUENCE
IDENTIFICATION OF THE SEQUENCE: P1
LENGTH: 26
TYPE: amino acid
CHAINING: only one chain
TOPOLOGY: lineal
TYPE OF MOLECULE: peptide
SEQUENCE:
 The sequence of amino acids of peptide P1 is in the following sequence:
VAPIAKYLATALAKWALKQGFAKLKS (SEQ ID NO: 1)

The entire disclosure of all publications (including patents, patent applications, journal articles, books, or other documents) cited herein are hereby incorporated by reference. It is understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A peptide of 26 amino acids, characterized for having the following amino acid sequence: VAPIAKYLATALAK-WALKQGFAKLKS (SEQ ID NO: 1) and pharmaceutically acceptable salts or derivatives thereof.

2. The peptide according to claim 1, characterized by exhibiting an antimicrobial and ionophoric activity.

3. The peptide according to claim 2, wherein the antimicrobial activity is against Gram-positive and Gram-negative bacteria.

4. The peptide according to claim 2, wherein the ionophoric activity is in the inner membrane of rat liver mitochondria.

5. A pharmaceutical composition comprising as active principle the peptide according to claim 1, together with a pharmaceutically acceptable carrier.

6. A pharmaceutical composition comprising as active principle the peptide according to claim 1 in an amount effective for inhibiting the microbial growth of Gram-positive or Gram-negative bacteria, together with a pharmaceutically acceptable carrier.

7. A pharmaceutical composition comprising as active principle the peptide according to claim 1, in an amount effective for exhibiting ionophoric activity, together with a pharmaceutically acceptable carrier.

8. A pharmaceutical composition according to claim 5 characterized by being presented in a form suitable for oral, topical, rectal or parenteral administration.

9. A composition for agricultural use comprising as active ingredient the peptide according to claim 1, together with an acceptable carrier.

10. A composition for agricultural use comprising as active ingredient the peptide according to claim 1, in an amount effective for inhibiting the microbial growth of Gram-positive or Gram-negative bacteria, together with an acceptable carrier.

11. A composition for agricultural use according to claim 9, characterized by being presented in a form suitable for its application in agriculture.

* * * * *

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: Synthetic peptide P1

<400> SEQUENCE: 1

Val Ala Pro Ile Ala Lys Tyr Leu Ala Thr Ala Leu Ala Lys Trp Ala
1               5                   10                  15

Leu Lys Gln Gly Phe Ala Lys Leu Lys Ser
            20                  25
```